(12) United States Patent
Liou et al.

(10) Patent No.: US 7,560,491 B2
(45) Date of Patent: Jul. 14, 2009

(54) Z-STILBENES DERIVATIVES AND THE PHARMACEUTICAL COMPOSITION THEREOF

(75) Inventors: Jing-Ping Liou, Taipei (TW);
Jang-Yang Chang, Taipei (TW)

(73) Assignees: Taipei Medical University (TW);
National Health Research Institutes (TW)

( * ) Notice: Subject to any disclaimer, the term of this patent is extended or adjusted under 35 U.S.C. 154(b) by 182 days.

(21) Appl. No.: 11/655,088

(22) Filed: Jan. 19, 2007

(65) Prior Publication Data

US 2008/0096973 A1      Apr. 24, 2008

(30) Foreign Application Priority Data

Oct. 19, 2006     (TW) ............... 95138548 A

(51) Int. Cl.
*A61K 31/075*      (2006.01)
*A61K 31/136*      (2006.01)
*C07C 211/45*     (2006.01)
*C07C 43/205*     (2006.01)

(52) U.S. Cl. .................. 514/648; 514/654; 514/716; 514/718; 514/721; 564/305; 568/586; 568/644; 568/645; 568/646

(58) Field of Classification Search .............. None
See application file for complete search history.

(56) References Cited

U.S. PATENT DOCUMENTS

| 4,996,237 A | 2/1991 | Pettit et al. .............. 514/720 |
| 5,430,062 A | 7/1995 | Cushman et al. ......... 514/646 |

FOREIGN PATENT DOCUMENTS

| JP | 07228558 A | 8/1995 |
| WO | WO 02/34244 A1 | 5/2002 |
| WO | WO 03/031381 A1 | 4/2003 |
| WO | WO 2006/036743 A1 | 4/2006 |

*Primary Examiner*—Rosalynd Keys
(74) *Attorney, Agent, or Firm*—Bacon & Thomas, PLLC

(57) ABSTRACT

A series of Z-stilbenes derivatives are disclosed, which have the structure as shown by formula 1. In the structure of formula 1, X is hydrogen, NHR, or nitro group, and R is hydrogen. Y and Z is independently hydrogen, halogen, $C_1$-$C_{10}$ alkyl, or $C_1$-$C_{10}$ alkoxyl. Furthermore, A is hydrogen, hydroxyl, or amino group. The compounds of the present invention have both aqueous solubility and anti-tumor activity. The Z-stilbenes derivatives of the present invention can further include a pharmaceutical carrier to form pharmaceutical compositions as potent anti-mitotic agents and anti-cancer agents.

24 Claims, No Drawings

Z-STILBENES DERIVATIVES AND THE PHARMACEUTICAL COMPOSITION THEREOF

BACKGROUND OF THE INVENTION

1. Field of the Invention

The present invention relates to a Z-stilbenes derivative and a pharmaceutical composition thereof, more particularly, to a Z-stilbenes derivative which can inhibit microtubules polymerization and a pharmaceutical composition thereof.

2. Description of Related Art

The microtubule system of eukaryotic cells is an important target for the development of anticancer agents. For a more concrete description, the microtubule polymerization/depolymerization is a popular target for the development of new chemotherapy agents. A number of clinically used agents (such as paclitaxel, epothilone A, vinblastine, combretastatin A-4 (CA-4), dolastatin 10, and colchicines), taking microtubule polymerization/depolymerization as the target, all exhibit their anticancer properties by disrupting cellular microtubule structure and function resulting in mitotic arrest, as well as inhibiting the growth of epithelium of newly formed vasculature to shut down the blood supply to tumors (please refer to Jordan et. al., (1998) Med. Res. Rev. 18: 259-296).

Therefore, according to the microtubule system (such as tubulin polymerization/depolymerization) as the target for developing compounds, the new therapy used for the treatment or the prevention of cancers or cancer related symptoms, or the treatment of angiogenesis related disease, such as cardiovascular disease (e.g. atherosclerosis), chronic inflammation (e.g. rheumatoid arthritis or Crohn's disease), diabetes (e.g. diabetic retinopathy), psoriasis, and retinal neovascularization or corneal neovascularization can be developed (please refer to Griggs rt. al., (2002) Am. J. Pathol. 160(3): 1097-1103).

It is discovered that colchicine and combretastatin A-4, such as the following ZD6126, CA4P, and AVE-8062, can exhibit the anticancer property by rapidly depolymerizing microtubules of newly formed vasculature to shut down the blood supply to tumors:

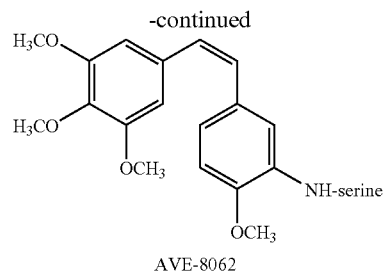

ZD 6126

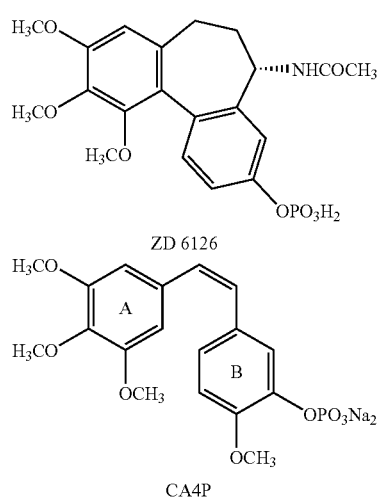

CA4P

-continued

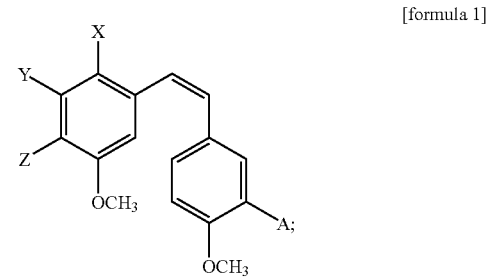

AVE-8062

The aforementioned compounds are now undergoing human clinical trials for either single use or combination use with chemotherapy drugs to inhibit cancers.

The analysis of Structure-Activity Relationship (SAR) can interpret the effect of the chemical structure on the activity so as to develop the most effective drugs to treat diseases. Through the analysis of SAR, it is found that the B ring of the aforementioned CA4P structure is the site on which the polar functional group(s) is often located. Thereby, new Z-stilbenes derivatives having anticancer activity can be developed by modifying the functional group(s) located on the B ring. In addition, the solubility of the CA-4 like compounds can be enhanced by introducing a phosphate group, amino group, or others. Therefore, considerable research focuses on developing novel Z-stilbenes derivatives different from conventional ones, having solubility, and exhibiting anticancer activity to afford a series of compounds, which can inhibit cancers.

SUMMARY OF THE INVENTION

The present invention relates to novel Z-stilbenes derivatives as the following formula 1:

[formula 1]

wherein, X is H, NHR, or nitro ($NO_2$), wherein R is H; Y and Z is independently H, halogen, $C_{1-10}$ alkyl, or $C_{1-10}$ alkoxyl; and A is H, OH, or amino.

Preferably, NHR is amino, Y is methoxy, and Z is methoxy. The halogen can be F, Cl, Br, or I, but preferably, the halogen is Br.

The term "alkyl" as used herein refers to a straight or branched saturated hydrocarbon chain containing from 1 to 10 carbon atoms. Representative examples of alkyl include, but are not limited to methyl, ethyl, n-propyl, isopropyl, tert-butyl, and n-pentyl.

The compounds of the present invention include 2-amino-3,4,4',5-tetramethoxy-stilbene, 2-nitro-3,4,4',5-tetramethoxy-stilbene, 2-amino-3,4',5-trimethoxy-stilbene, 2-amino-4,4',5-trimethoxy-stilbene, 3-bromo-4,4',5-triamethoxy-stilbene, 2-amino-3'-hydroxy-3,4,4',5-tetramethoxy-stilbene, and 2,3'-diamino-3,4,4',5-tetramethoxy-stilbene.

A non-aromatic double bond and one or more asymmetric centers may exist in the Z-stilbenes derivatives of the present invention. The chemical structure depicted herein encompasses meso compounds, racemic mixtures, enantiomers, diastereomers, diastereomer mixtures, cis-isomers, and trans-isomers. The present invention encompasses all isomeric forms, including E-form isomers, and Z-form isomers.

The application field of the Z-stilbenes derivatives of the present invention is not limited. Preferably, the Z-stilbenes derivatives of the present invention are used for inhibiting tubulin polymerization, and tubulin polymerization related cancers or angiogenesis related diseases.

In addition, the present invention further provides a pharmaceutical composition, comprising the Z-stilbenes derivative of the present invention and a pharmaceutically acceptable carrier to inhibit tubulin polymerization, or tubulin polymerization related cancers or diseases.

The Z-stilbenes derivatives of the present invention encompass the compounds themselves, their pharmaceutically acceptable salts, and prodrugs thereof. For example, the salt can be prepared by reacting the positive group (such as amino) of the compound with an anion. The satiable anions include, but are not limited to chloride, bromide, iodide, sulfate, nitrate, phosphate, citrate, alkylsulfonate, trifluoroacetate, and acetate. Also, the salt can be prepared by reacting the negative group (such as carboxy) with a cation. The satiable cations include, but are not limited to sodium, potassium, magnesium, calcium, and ammonium (such as tetramethylammonium). The examples of the prodrugs include the ester derivatives derived from the aforementioned compounds and other pharmaceutically acceptable derivatives.

The pharmaceutical composition comprising the Z-stilbenes derivatives of the present invention can be administered intravenously, orally, nasally, rectally, locally, or sublingually. Intravenous administration includes subcutaneous, intraperitoneal, intravenous, intramuscular, intraarticular, intraaortic, intrapleural, spinal, intrathecal, local injection at the site attacked by a disease, or other suitable administration techniques.

The sterile injectable composition can be a solution, or suspension in a non-toxic intravenous diluent or solvent (such as 1,3-butanediol). The acceptable carrier or solvent can be mannitol or water. In addition, the fixed oil is conventionally employed as a solvent or suspending medium (such as synthetic mono- or diglycerides). [I feel the following sentence would be slightly better as "Use of the fatty acid . . . is found in the operation . . . " as an acid probably cannot find any use.]>The fatty acid such as oleic acid and the glycerine ester derivative thereof find use in the preparation of pharmaceutically acceptable injectables, such as olive oil or castor oil, especially in polyoxyethylated form. The oily solution or suspension can comprise long chain aliphatic alcohol diluents or dispersion, carboxymethylcellulose, or a similar dispersion. Examples of the generally used materials include surfactants (e.g. Tween, or Spans), other similar emulsifying agents, pharmaceutically acceptable solid, liquid generally used in the pharmaceutical industry, or other bioavailable potentiating agents used for developing new formulations.

The pharmaceutical composition may be in a form suitable for oral use, for example, as capsule, troche, emulsifying agent, liquid suspension, dispersion, or solvent. For administration in a troche form, the generally used carrier is lactose or corn starch, flotation reagent (e.g. magnesium stearate as an elementary additive). For oral administration in a capsule form, the useful diluents include lactose and corn starch. For oral administration in a liquid suspension or emulsifying agent, the active material can be suspended or dissolved in an oily medium containing an emulsifying agent or suspension. If necessary, suitable sweetening agents, flavoring agents, or coloring agents can be added.

Compositions intended for nasal aerosol or inhalation may be prepared according to any method known to the art for the manufacture of pharmaceutical compositions. For example, the composition prepared in the isotonic sodium chloride solution can further contain benzyl alcohol or other suitable preservative, an absorbefacient to enhance bioavailability, fluorocarbon, or other known soluble dispersion. The compositions comprising one or more active compounds of the present invention may also be administered in the form of suppositories for rectal administration of the drug.

The carrier of the pharmaceutical composition containing the Z-stilbenes derivative must be acceptable. The term "acceptable" means the carrier is compatible with the active ingredient (more preferably, the carrier can stabilize the active ingredient), and does not hurt the patient. One or more agents can be a pharmaceutical elixir which can deliver the active compound of the present invention. Examples of other carriers include silicon oxide, magnesium stearate, cellulose, sodium lauryl sulfate, and D&C Yellow 10.

BRIEF DESCRIPTION OF THE DRAWINGS

None.

DETAILED DESCRIPTION OF THE PREFERRED EMBODIMENT

The Z-stilbenes derivatives of the present invention, the analysis method thereof, and the determination method thereof are presented in the following:

Melting points were determined on a Büchi (B-545) melting point apparatus and are uncorrected.

Nuclear magnetic resonance ($^1$H NMR and $^{13}$C NMR) spectra were obtained with the Bruker DRX-500 spectrometer (operating at 500 MHz and at 125 MHz, respectively), Varian Mercury-400 spectrometer (operating at 400 MHz and at 100 MHz, respectively), and the Varian Mercury-300 spectrometer (operating at 300 MHz and at 75 MHz, respectively), with chemical shift in parts per million (ppm,$\delta$) downfield from TMS as an internal standard.

High-resolution mass spectra (HRMS) were measured with a Finnigan (MAT-95XL) electron impact (EI) mass spectrometer.

Elemental analyses were performed on a Heraeus CHN-O Rapid microanalyzer.

Flash column chromatography was done using silica gel (Merck Kieselgel 60, No. 9385, 230-400 mesh ASTM).

All reactions were carried out under an atmosphere of dry nitrogen.

The preparation involved a reaction sequence (overall 30-46% yield in two or three steps): (1) Wittig reaction of (4-methoxybenzyl)phosphonium bromide (scheme 1) and (2-nitro-3,4,5-trimethoxybenzyl)phosphonium bromide (scheme 2), with various substituted benzaldehydes including 2-nitro or 3-nitrobenzaldehydes yielded the corresponding Z- and E-stilbenes as an about ratio of 3/1. (2) Reduction of nitro group of Z-stilbenes by Zn/AcOH to afford the desired substituted 2-amino and 2'-aminocombretastatins derivatives. Ylide (compound B2) was synthesized from the 2-nitro-3,4,5-trimethoxybenzyl bromide (compound B1). The methoxy-substituted benzaldehydes A3-A6, and B3 are commercially available. The 2-nitrobenzaldehydes A1-A2 and 3-(tert-butyldimethylsilyl) protected isovanillin B4 were prepared in two-four steps.

The synthetic schemes of the compounds of the present invention and the prodrugs thereof are shown in the following.

Scheme 1

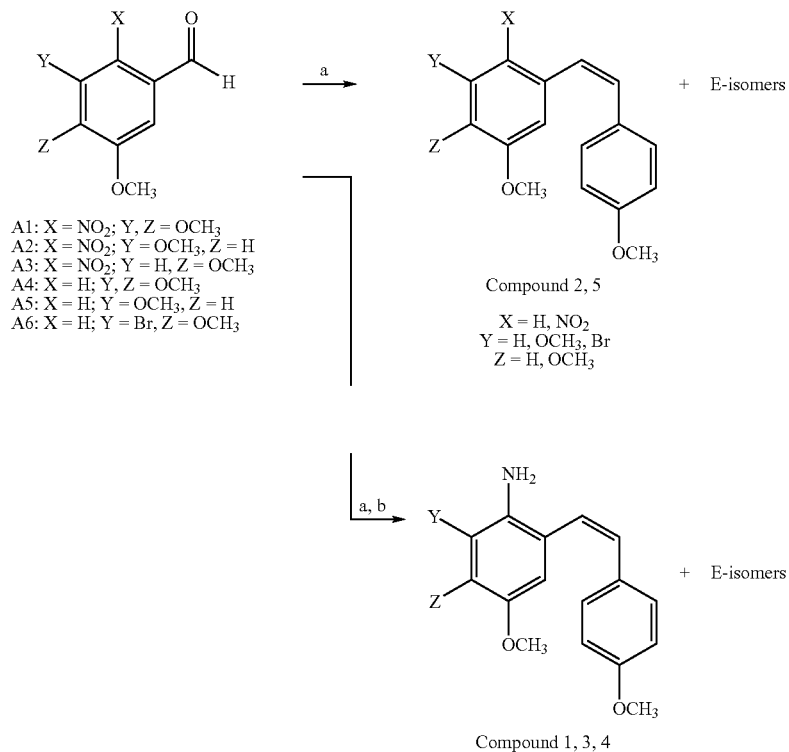

A1: X = NO$_2$; Y, Z = OCH$_3$
A2: X = NO$_2$; Y = OCH$_3$, Z = H
A3: X = NO$_2$; Y = H, Z = OCH$_3$
A4: X = H; Y, Z = OCH$_3$
A5: X = H; Y = OCH$_3$, Z = H
A6: X = H; Y = Br, Z = OCH$_3$

Compound 2, 5
X = H, NO$_2$
Y = H, OCH$_3$, Br
Z = H, OCH$_3$

Compound 1, 3, 4

Reagent and Condition:
a. (4-methoxybenzyl)triphenylphosphonium bromide, n-BuLi, THF, -78° C.
b. Zn, AcOH, room temperature Scheme 2

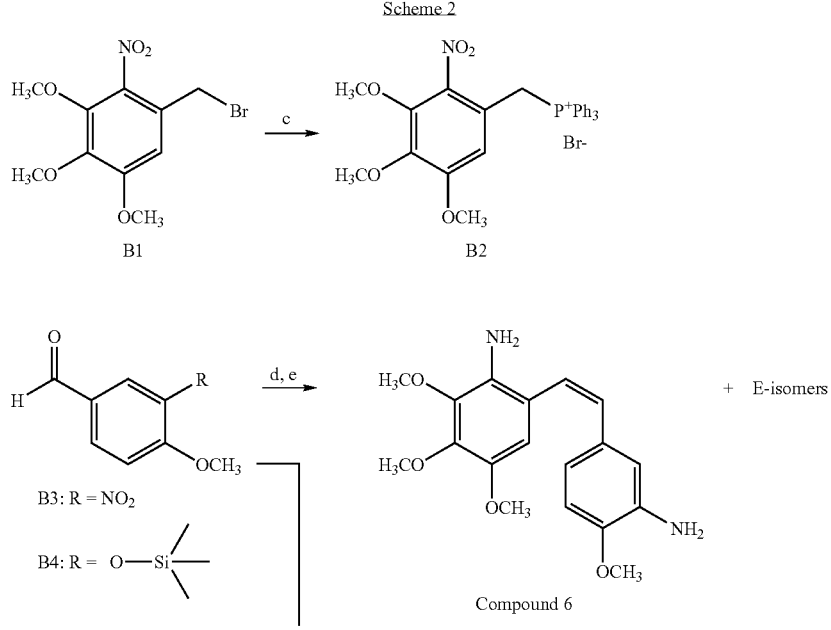

B1
B2
B3: R = NO$_2$
B4: R = O—Si

Compound 6

-continued

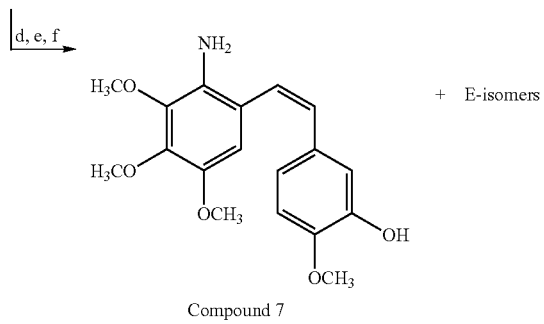

Compound 7

+ E-isomers

Reagent and Condition:
c. PPh₃, toluene, reflux
d. B2, n-BuLi, THF, -78° C.
e. Zn, AcOH, room temperature
f. tetra-n-butylammonium floride, THF, room temperature

EXAMPLES OF PREPARATION

Compound A1: 2-Nitro-3,4,5-trimethoxy-benzaldehyde

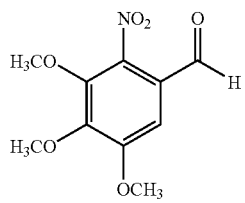

Compound A1

To a stirred solution of the 3,4,5-Trimethoxy-2-nitrobenzoic acid (2 g, 7.77 mmol) and $BH_3$ (1.0 M in THF, 13.2 ml) in THF (10 ml) was stirred and refluxed for 3 hours. After cooling, the reaction mixture was extracted with water and $CH_2Cl_2$. The combined organic layers were dried over $MgSO_4$, and then evaporated to afford 4-methoxy-2-nitrobenzyl methanol. The crude 4-methoxy-2-nitrobenzyl methanol was dissolved in anhydrous $CH_2Cl_2$ (20 mL) and was subjected to pyridinium dichromate, PDC oxidation (5.84 g, 15.55 mmol)/molecular sieves (powder, 6 g) at room temperature for 16 h. The reaction mixture was filtrated by Celite and extracted with water and $CH_2Cl_2$. The organic layers were combined and evaporated. The residue was purified by flash chromatography (EtOAc:n-hexane=1:1) to afford compound A1 as a yellow solid, yield 69%. mp 73.8-75.1° C., $^1$H NMR (500 MHz, $CDCl_3$) δ 3.97 (s, 3H), 3.99 (s, 6H), 7.21 (s, 1H), 9.86 (s, 1H).

Compound A2: 3,5-Dimethoxy-2-nitro-benzaldehyde

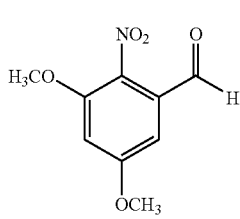

Compound A2

The 3,5-Dimethoxybenzaldehyde (0.5 g, 3 mmol) was added to 70% nitric acid (0.88 mL, 14.44 mmol) at 0° C. in portion. After stirring for 1 hour, the reaction mixture was quenched and extracted by water and $CH_2Cl_2$. The organic layers were combined and evaporated to give a residue, which was purified by flash chromatography (EtOAc:n-hexane=1:2.5) to give the brown crystals, yield 64%. mp 104.0-104.6° C., $^1$H NMR (500 MHz, $CDCl_3$) δ 3.93 (s, 3H), 3.93 (s, 3H), 6.76 (d, J=2.4 Hz), 6.96 (d, J=2.4 Hz, 1H), 9.94 (s, 1H).

Compound B1: 2-Nitro-3,4,5-trimethoxybenzyl bromide

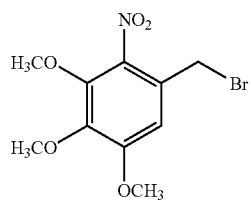

Compound B1

To a stirred solution of the 3,4,5-Trimethoxy-2-nitrobenzoic acid (5 g, 19.40 mmol) in THF (30 ml) was added by $BH_3$ (1.0 M in THF, 29.1 ml) under nitrogen. The mixture was stirred and refluxed for 2 hours. After cooling, the reaction mixture was extracted with water and $CH_2Cl_2$. The combined organic layers were dried over MgSO$_4$, and then evaporated to afford 3,4,5-Trimethoxy-2-nitrobenzyl methanol. The crude 3,4,5-trimethoxy-2-nitrobenzyl methanol was dissolved in anhydrous CH$_2$Cl$_2$ (20 mL) and was subjected to PBr$_3$ (2.40 ml, 25.22 mmol) in an ice bath. After 2 h, the mixture was extracted with water and CH$_2$Cl$_2$. The organic layers were combined and evaporated. The residue was purified by flash chromatography (EtOAc:n-hexane=1:2) to afford B1 as a pale yellow oil, yield 68%. $^1$H NMR (500 MHz, CDCl$_3$) δ 3.90 (s, 3H), 3.92 (s, 3H), 3.98 (s, 3H), 4.44 (s, 2H), 6.72 (s, 1H).

Compound B2: 2-Nitro-3,4,5-trimethoxybenzyl-triphenylphosphonium bromide

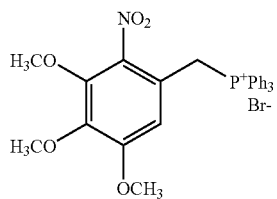

Compound B2

To a stirred suspension of B1 (4 g, 13.06 mmol) and triphenylphosphine (3.77 g, 14.37 mmol) in anhydrous toluene (50 ml) was heated to reflux for 3-5 hr under N$_2$. After cooling, the reaction mixture was filtrated, and recrystallized from CH$_3$OH to give B2 as a pale yellow powder, yield 74%. mp 173-174° C., $^1$H NMR (500 MHz, CDCl$_3$) δ 3.70 (s, 3H), 3.83 (s, 3H), 3.84 (s, 3H), 5.56 (d, J=14.0 Hz, 2H), 7.34 (d, J=2.4 Hz, 1H), 7.72 (m, 15H).

Compound B4: 3-(tert-Butyl-dimethyl-silyloxy)-4-methoxy-benzaldehyde

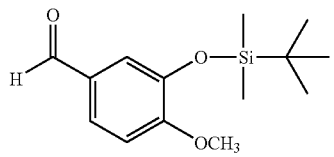

Compound B4

To a solution of 3-hydroxy-4-methoxybenzaldehyde (1 g, 6.57 mmol) and N,N-diisopropylethylamine (1.32 mL, 9.86 mmol) in THF (20 mL) was stirred at room temperature. After stirring for 30 min, tert-butyl-dimethyl-silylchloride (1.19 g, 7.88 mmol) was added then stirred for 3 h. The reaction mixture was extracted with water and CH$_2$Cl$_2$. The organic layers were combined and evaporated to afford B4 as a yellow solid, yield 92%. $^1$H NMR (500 MHz, CDCl$_3$) δ 0.15 (s, 6H), 0.99 (s, 9H), 3.87 (s, 3H), 6.94 (d, J=8.2 Hz, 1H), 7.35 (d, J=2.0 Hz, 1H), 7.45 (dd, J=8.3, 2.0 Hz, 1H).

Example 1

2-Amino-3,4,4',5-tetramethoxy-(Z)-stilbene (compound 1)

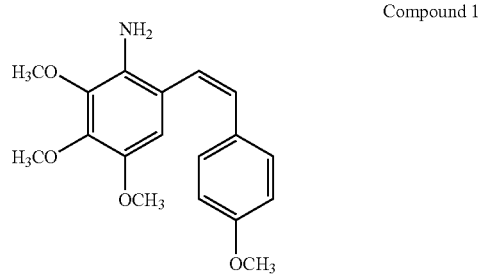

Compound 1

The title compound was obtained in 39% overall yield from (4-methoxybenzyl)triphenylphosphonium bromide and 2-nitro-3,4,5-trimethoxybenzaldehyde (compound A1). $^1$H NMR (500 MHz, CD$_3$OD) δ 3.52 (s, 3H), 3.73 (s, 3H), 3.82 (s, 3H), 3.83 (s, 3H), 6.35 (d, J=11.9 Hz, 1H), 6.45 (s, 1H), 6.55 (d, J=12.0 Hz, 1H), 6.74 (d, J=8.6 Hz, 2H), 7.15 (d, J=8.6 Hz, 2H). $^{13}$C NMR (125 MHz, CD$_3$OD) δ 55.6, 56.9, 60.8, 61.3, 110.3, 114.5, 120.0, 125.0, 130.8, 131.2, 131.4, 133.6, 142.8, 143.4, 146.6, 160.4. MS (EI) m/z: 315 (M$^+$, 100%), 300 (58%). HRMS (EI) for C$_{18}$H$_{21}$NO$_4$ (M$^+$): calcd, 315.1469; found, 315.1470. Anal. (C$_{18}$H$_{21}$NO$_4$) C, H, N.

Example 2

2-Nitro-3,4,4',5-tetramethoxy-(Z)-stilbene (compound 2)

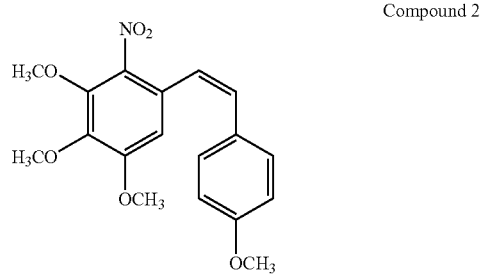

Compound 2

The title compound was obtained in 53% overall yield from 4-trimethoxybenzyl-triphenylphosphonium bromide and 3,4,5-trimethoxy-2-nitrobenaldehyde (compound A1). $^1$H NMR (500 MHz, CDCl$_3$) δ 3.56 (s, 3H), 3.78 (s, 3H), 3.89 (s, 3H), 3.99 (s, 3H), 6.35 (d, J=12.0 Hz, 1H), 6.50 (s, 1H), 6.66 (d, J=12.0 Hz, 1H), 6.76 (d, J=8.5 Hz, 2H), 7.12 (d, J=8.5 Hz, 2H). MS (EI) m/z: 345 (M$^+$, 71%), 194 (100%). HRMS (EI) for C$_{18}$H$_{19}$NO$_6$ (M$^+$): calcd, 345.1202; found, 345.1207.

Example 3

2-Amino-3,4',5-trimethoxy-(Z)-stilbene (compound 3)

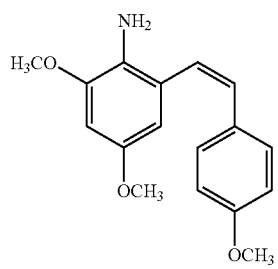

Compound 3

The title compound was obtained in 40% overall yield from (4-methoxybenzyl)triphenylphosphonium bromide and 3,5-dimethoxy-2-nitrobenzaldehyde (compound A2); mp 83.2-86.3° C. $^1$H NMR (500 MHz, CDCl$_3$) δ 3.63 (s, 3H), 3.75 (s, 3H), 3.83 (s, 3H), 6.31 (d, J=2.3 Hz, 1H), 6.39 (s, 1H), 6.41 (d, J=12.9 Hz, 1H), 6.58 (d, J=12.0 Hz, 1H), 6.73 (d, J=8.7 Hz, 2H), 7.19 (d, J=8.7 Hz, 2H). $^{13}$C NMR (125 MHz, CDCl$_3$) δ 55.0, 55.5, 98.4, 103.9, 113.4, 123.5, 124.2, 127.2, 129.2, 130.0, 130.8, 148.4, 152.1, 158.8. MS (EI) m/z: 285 (M$^+$, 100%), 270 (29%). HRMS (EI) for C$_{17}$H$_{19}$NO$_3$ (M$^+$): calcd, 285.1369; found, 285.1367. Anal. (C$_{17}$H$_{19}$NO$_3$) C, H, N.

Example 4

2-Amino-4,4',5-trimethoxy-(Z)-stilbene (compound 4)

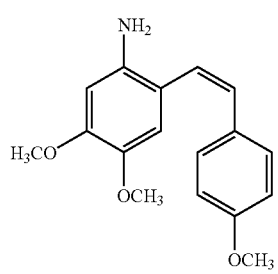

Compound 4

The title compound was obtained in 43% overall yield from 4-trimethoxybenzyl-triphenylphosphonium bromide and 6-nitroveratraldehyde (compound A3). mp 62.7-63.8° C., $^1$H NMR (500 MHz, CDCl$_3$) δ 3.65 (s, 3H), 3.76 (s, 3H), 3.84 (s, 3H), 6.28 (s, 1H), 6.34 (d, J=12.0 Hz, 1H), 6.52 (d, J=12.0 Hz, 1H), 6.64 (s, 1H), 6.74 (dd, J=8.8, 2.0 Hz, 2H), 7.20 (dd, J=8.8, 2.0 Hz, 2H). $^{13}$C NMR (125 MHz, CDCl$_3$) δ 55.1, 55.6, 56.2, 100.4, 113.0, 113.5, 114.6, 124.0, 129.4, 130.0, 130.1, 137.6, 141.8, 149.2, 158.7. MS (EI) m/z: 285 (M$^+$, 100%), 270 (47%). HRMS (EI) for C$_{17}$H$_{19}$NO$_3$ (M$^+$): calcd, 285.1373; found, 285.1369.

Example 5

3-Bromo-4,4',5-trimethoxy-(Z)-stilbene (compound 5)

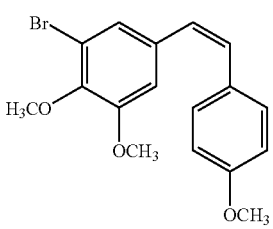

Compound 5

The title compound was obtained in 45% overall yield from 4-trimethoxybenzyl-triphenylphosphonium bromide and 5-bromoveratraldehyde (compound A6). $^1$H NMR (300 MHz, CDCl$_3$) δ 3.61 (s, 3H), 3.77 (s, 3H), 3.87 (s, 3H), 6.35 (d, J=12.0 Hz, 1H), 6.53 (d, J=12.0 Hz, 1H), 6.77 (d, J=1.2 Hz, 1H), 6.79 (d, J=8.6 Hz, 2H), 7.05 (d, J=1.1 Hz, 1H), 7.20 (d, J=8.6 Hz, 2H). $^{13}$C NMR (75 MHz, CDCl$_3$) δ 55.1, 55.7, 60.5, 111.9, 113.5, 117.2, 125.1, 126.9, 129.0, 130.1, 130.4, 134.5, 145.2, 153.0, 158.8. MS (EI) m/z: 350 (M$^+$, 98%), 348 (100%). HRMS (EI) for C$_{17}$H$_{17}$BrO$_3$ (M$^+$): calcd, 350.0312; found, 350.0340.

Example 6

2-Amino-3'-hydroxy-3,4,4',5-tetramethoxy-(Z)-stilbene (compound 6)

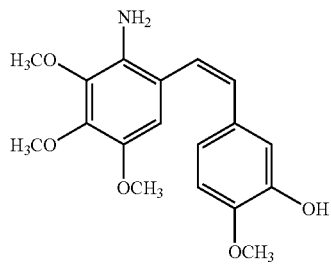

Compound 6

The title compound was obtained in 30% overall yield from 2-nito-(3,4,5-trimethoxybenzyl)triphenylphosphonium bromide (compound B2) and 3-(tert-butyldimethylsilyloxy)-4-methoxybenzaldehyde (compound B4) according to the above procedure and one extra procedure, which was 3 equiv of tetra-n-butylammonium floride/THF at room temperature stirring 1 h. $^1$H NMR (500 MHz, CD$_3$OD) δ 3.55 (s, 3H), 3.79 (s, 3H), 3.82 (s, 3H), 3.83 (s, 3H), 6.33 (d, J=12 Hz, 1H), 6.49 (s, 1H), 6.50 (d, J=11.9 Hz, 1H), 6.71 (dd, J=8.2, 1.9 Hz, 1H), 6.74 (d, J=1.8 Hz, 1H), 6.77 (d, J=8.2 Hz, 1H). $^{13}$C NMR (125 MHz, CD$_3$OD) δ 56.3, 57.0, 60.9, 61.3, 110.4, 112.3, 116.5, 120.0, 122.0, 125.1, 131.4, 131.5, 133.5, 142.9, 143.4, 146.7, 147.1, 148.5. MS (EI) m/z: 331 (M$^+$, 100%), 284 (25%). HRMS (EI) for C$_{18}$H$_{21}$NO$_5$ (M$^+$): calcd, 331.1422; found, 331.1421. Anal. (C$_{18}$H$_{21}$NO$_5$) C, H, N.

Example 7

2,3'-Diamino-3,4,4',5-tetramethoxy-(Z)-stilbene (compound 7)

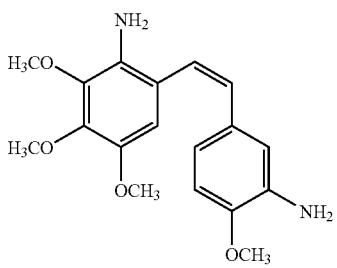

Compound 7

The title compound was obtained in 34% overall yield from 2-nito-3,4,5-(trimethoxybenzyl)triphenylphosphonium bromide (compound B2) and 4-methoxy-3-nitrobenzaldehyde (compound B3). mp 97.3-98.1° C. $^1$H NMR (500 MHz, Acetone-$d_6$) δ 3.54 (s, 3H), 3.77 (s, 3H), 3.79 (s, 3H), 3.80 (s, 3H), 4.01 (s, 2H), 4.25 (s, 2 H), 6.26 (d, J=12.1 Hz), 6.39 (d, J=12.1 Hz, 1H), 6.53 (s, 1H), 6.56 (dd, J=8.2, 1.7 Hz, 1H), 6.66 (d, J=8.2 Hz, 1H), 6.68 (d, J=1.8 Hz, 1H). $^{13}$C NMR (125 MHz, Acetone-$d_6$) δ 56.1, 57.1, 61.0, 61.4, 110.5, 111.2, 117.0, 120.4, 120.9, 124.9, 131.3, 132.1, 133.6, 137:3, 143.0, 143.5, 146.8, 148.8. MS (EI) m/z: 330 (M$^+$, 100%), 315 (27%). HRMS (EI) for $C_{18}H_{22}N_2O_4$ (M$^+$): calcd, 330.1578; found, 330.1570. Anal. ($C_{18}H_{22}N_2O_4$) C, H, N.

Example 8

Biological Test (a) Material

Regents for cell culture were obtained from Gibco-BRL Life Technologies (Gaithersburg, Md.). Microtubule-associated protein (MAP)-rich tubulin was purchased from Cytoskeleton, Inc. (Denver, Colo.). [$^3$H]Colchicine (specific activity, 60-87 Ci/mmol) was purchased from PerkinElmer Life Sciences (Boston, Mass.).

(b) Cell Growth Inhibitory Assay

Human oral epidermoid carcinoma KB cells, colorectal carcinoma HT29 cells, non small cell lung carcinoma H460 cells, and two stomach carcinoma TSGH, MKN45 cells were maintained in RPMI-1640 medium supplied with 5% fetal bovine serum.

KB-VIN10 cells were maintained in growth medium supplemented with 10 nM vincristine, generated from vincristine-driven selection, and displayed overexpression of P-gp170/MDR.

Cells in logarithmic phase were cultured at a density of 5000 cells/mL/well in a 24-well plate. KB-VIN10 cells were cultured in a drug-free medium for 3 days prior to use. The cells were exposed to various concentrations of the test drugs for 72 hours. The methylene blue dye assay was used to evaluate the effect of the test compounds on cell growth as described previously.1 The IC$_{50}$ value resulting from 50% inhibition of cell growth was calculated graphically as a comparison with the control.

The result of the examination shows that among the compounds 1-7 of the present invention, IC$_{50}$ of at least five compounds is <5 μM, and IC$_{50}$ of the other compounds is <50 nM.

(c) Tubulin Polymerization in Vitro Assay

Turbidimetric assays of microtubules were performed as described by Bollag et al.

MAP-rich tubulin (2 mg/mL) in 100 μL buffer containing 100 mM PIPES (pH 6.9), 2 mM MgCl$_2$, 1 mM GTP, and 2% (v/v) dimethyl sulfoxide were placed in 96-well microtiter plate in the presence of test compounds. The increase in absorbance was measured at 350 nm in a PowerWave X Microplate Reader (BIO-TEK Instruments, Winooski, Vt.) at 37° C. and recorded every 30 sec for 30 min. The area under the curve (AUC) was used to determine the concentration that inhibited tubulin polymerization to 50% (IC$_{50}$). The AUC of the untreated control and 10 μM of colchicine was set to 100% and 0% polymerization, respectively, and the IC$_{50}$ was calculated by nonlinear regression in at least three experiments.

According to the results, the tested stilbenes derivatives (<5 μM, in the average) exhibit the property of inhibiting microtubulin polymerization.

Although the present invention has been explained in relation to its preferred embodiment, it is to be understood that many other possible modifications and variations can be made without departing from the scope of the invention as hereinafter claimed.

What is claimed is:

1. A Z-stilbenes compound as the following formula (1):

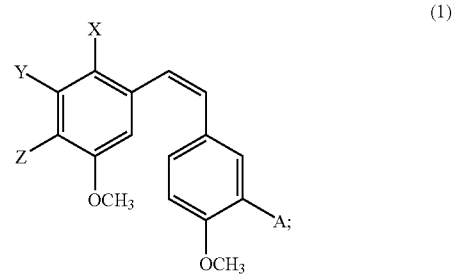

(1)

wherein, X is H, NHR, or nitro (NO$_2$), wherein R is H; Y and Z is independently H, halogen, $C_{1-10}$ alkyl, or $C_{1-10}$ alkoxyl; and A is H, OH, or amino, with the proviso that X is not H when Y is $C_{1-10}$ alkoxyl and A is H or OH.

2. The compound as claimed in claim 1, wherein NHR is amino.

3. The compound as claimed in claim 1, wherein Y is methoxy.

4. The compound as claimed in claim 1, wherein Z is methoxy.

5. The compound as claimed in claim 1, wherein the halogen is F, Cl, Br, or I.

6. The compound as claimed in claim 1, wherein the halogen is Br.

7. The compound as claimed in claim 1, wherein the compound is 2-amino-3,4,4',5-tetramethoxy-stilbene.

8. The compound as claimed in claim 1, wherein the compound is 2-nitro-3,4,4',5-tetramethoxy-stilbene.

9. The compound as claimed in claim 1, wherein the compound is 2-amino-3,4',5-trimethoxy-stilbene.

10. The compound as claimed in claim 1, wherein the compound is 2-amino-4,4',5-trimethoxy-stilbene.

11. The compound as claimed in claim 1, wherein the compound is 3-bromo-4,4',5-triamethoxy-stilbene.

12. The compound as claimed in claim 1, wherein the compound is 2-amino-3'-hydroxy-3,4,4',5-tetramethoxy-stilbene.

13. The compound as claimed in claim 1, wherein the compound is 2,3'-diamino-3,4,4',5-tetramethoxy-stilbene.

14. The compound as claimed in claim 1, wherein the compound is used for inhibiting cellular microtubule polymerization.

15. The compound as claimed in claim 1, wherein the compound is used for inhibiting a microtubule polymerization related cancer.

16. A pharmaceutical composition, comprising a compound as the following formula (1):

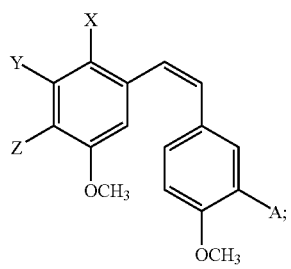

(1)

wherein, X is H, NHR, or nitro ($NO_2$), wherein R is H; Y and Z is independently H, halogen, $C_{1-10}$ alkyl, or $C_{1-10}$ alkoxyl; and A is H, OH, or amino, with the proviso that X is not H when Y is $C_{1-10}$ alkoxyl and A is H or OH; and a pharmaceutically acceptable carrier.

17. The pharmaceutical composition as claimed in claim 16, wherein Y is methoxy.

18. The pharmaceutical composition as claimed in claim 16, wherein Z is methoxy.

19. The pharmaceutical composition as claimed in claim 16, wherein X is amino.

20. The pharmaceutical composition as claimed in claim 16, wherein the halogen is F, Cl, Br, or I.

21. The pharmaceutical composition as claimed in claim 16, wherein the halogen is Br.

22. The pharmaceutical composition as claimed in claim 16, wherein the compound is 2-amino-3,4,4',5-tetramethoxy-stilbene, 2-nitro-3,4,4',5-tetramethoxy-stilbene, 2-amino-3,4',5-triamethoxy-stilbene, 2-amino-4,4',5-triamethoxy-stilbene, 3-bromo-4,4',5-triamethoxy-stilbene, 2-amino-3'-hydroxy-3,4,4',5- tetramethoxy-stilbene, or 2,3'-diamino-3,4,4',5-tetramethoxy-stilbene.

23. The pharmaceutical composition as claimed in claim 16, wherein the compound is used for inhibiting cellular microtubule polymerization.

24. The pharmaceutical composition as claimed in claim 16, wherein the compound is used for inhibiting a microtubule polymerization related cancer.

* * * * *